(12) United States Patent
McClelland

(10) Patent No.: US 6,583,618 B2
(45) Date of Patent: Jun. 24, 2003

(54) REMOTE MAGNETIC FIELD MATERIAL ANALYZER AND METHOD

(75) Inventor: Richard McClelland, Richland, WA (US)

(73) Assignee: Framatome, ANP Inc., Lynchburg, VA (US)

( * ) Notice: Subject to any disclaimer, the term of this patent is extended or adjusted under 35 U.S.C. 154(b) by 0 days.

(21) Appl. No.: 09/960,214

(22) Filed: Sep. 21, 2001

(65) Prior Publication Data

US 2003/0057943 A1 Mar. 27, 2003

(51) Int. Cl.[7] .................. G01N 27/72; G01N 27/90; G01R 33/12; G21C 17/00
(52) U.S. Cl. .................. 324/239; 324/240; 376/245; 376/259
(58) Field of Search ................ 324/219–221, 324/233, 239–243; 376/245, 249–251, 257, 259

(56) References Cited

U.S. PATENT DOCUMENTS

| | | | |
|---|---|---|---|
| 2,124,579 A | * 7/1938 | Knerr et al. ............ 324/220 X |
| 3,060,377 A | * 10/1962 | Schmidt ............ 324/220 |
| 3,619,771 A | * 11/1971 | Hentschel ............ 324/239 |
| 4,026,142 A | 5/1977 | Jacobs ............ 73/67.4 |
| 4,243,939 A | * 1/1981 | Grossman et al. ............ 324/239 X |
| 4,335,352 A | * 6/1982 | Stephen ............ 324/239 X |
| 5,028,100 A | * 7/1991 | Valleau et al. ............ 324/233 X |
| 5,262,726 A | 11/1993 | Kohmura et al. ............ 324/232 |
| 5,293,119 A | 3/1994 | Podney ............ 324/242 |
| 5,311,127 A | * 5/1994 | Bisiaux ............ 324/242 X |
| 5,315,243 A | 5/1994 | Kempster et al. ............ 324/204 |
| 5,467,014 A | 11/1995 | Nix ............ 324/230 |
| 5,574,368 A | 11/1996 | Horn et al. ............ 324/228 |
| 5,608,315 A | 3/1997 | Crayton et al. ............ 324/232 |
| 5,608,316 A | 3/1997 | Crayton et al. ............ 324/204 |
| 5,610,515 A | 3/1997 | Soules ............ 324/209 |
| 5,623,203 A | * 4/1997 | Hosohara et al. ............ 324/220 |
| 5,811,970 A | * 9/1998 | Cook et al. ............ 324/233 |
| 5,963,030 A | * 10/1999 | Stark ............ 324/239 X |
| 6,271,670 B1 | 8/2001 | Caffey ............ 324/642 |

FOREIGN PATENT DOCUMENTS

| JP | 62142258 | 6/1987 |
|---|---|---|
| JP | 2001141698 | 5/2001 |

OTHER PUBLICATIONS

Schmidt, T.R., "History of the Remote–Field Eddy Current Inspection Technique", Back to Basics, Materials Evaluation/47/, Jan. 1989.*

* cited by examiner

Primary Examiner—Gerard R. Strecker
(74) Attorney, Agent, or Firm—Kenyon & Kenyon

(57) ABSTRACT

The present invention provides an apparatus and method for measuring nonferrous electrical resistance measurement. The method includes providing a nonferrous material, inducing a magnetic field on the nonferrous material, measuring the remote magnetic field of the nonferrous material, and comparing the measured remote magnetic field to a standard.

15 Claims, 5 Drawing Sheets

103 ppm 496 ppm 1089 ppm

REMOTE MAGNETIC FIELD MATERIAL ANALYZER AND METHOD

FIELD OF THE INVENTION

The present invention relates to an apparatus and method to measure material resistance in nonferrous materials. More specifically, the invention relates to an apparatus and method to non-destructively measure resistance and changes in resistance in nonferrous materials using remote field eddy current technology.

BACKGROUND INFORMATION

Material analysis at nuclear facilities, such as nuclear electrical generating stations, is becoming increasingly critical to plant and personnel safety. Special materials are often selected for use in nuclear facilities to solve varied design problems. The special materials selected must often withstand forces developed from temperature fluctuation, radiation exposure, pressure, and other factors.

Failure to detect problems in these special materials can have varied consequences. These consequences include causing a station forced outage, equipment malfunction, material damage, radiation exposure to workers and extended maintenance outages. The potential severe consequences to safety as well as economic concerns from shutting down a nuclear electrical generating station necessitate minimization of material defects. Consequently, accurate and reliable analysis techniques are needed to ensure material viability used in nuclear operations.

Exposure to radiation causes certain materials to undergo changes in atomic structure and composition. A typical example of this is inclusion of hydrogen into non-ferrous materials. The inclusion of hydrogen into nonferrous materials can result in a loss of material ductility as well as changes to the materials electrical resistance.

The ductility of materials is often relied on to counteract the effects of a design basis accident, such as a loss of coolant accident, seismic event or pressure transient. When possible, ascertaining hydrogen content in a material allows maintenance personnel to assess the necessity of replacing or retiring a material from service. Thus, maintenance personnel use these assessments to verify conformance of installed equipment to original design specifications.

One of the most important components in a nuclear electrical generating station is a nuclear fuel assembly. Nuclear fuel assemblies usually consist of uranium based fuel pellets surrounded by a protective cladding. The cladding typically used is a nonferrous material, usually a type of zirconium alloy. The use of zirconium alloys provides both mechanical and chemical protection for the fuel pellets. Cladding materials must have excellent corrosion resistance, ductility, and the ability to withstand wide variations in temperature. In an operating nuclear electrical generating station, the cladding undergoes intense exposure to radiation throughout its service life. This intense exposure can be for prolonged cycles, in some instances 24 months between maintenance periods. When exposed this high radiation, zirconium alloys accumulate hydrogen into the alloy matrix.

To quantify the amount of hydrogen in a material used in a high radiation area, current practice requires removal of the material from service. Following removal from service, the material is placed into a facility known as a "hot cell". While in the "hot cell", the material is destructively tested to determine the hydrogen content.

Current destructive measurement processes can accurately measure the amount of hydrogen in the material, however certain drawbacks are readily apparent. Current processes require removal of the material from service and shipping to a specially equipped "hot cell" laboratory. When the material is destructively tested, the material is no longer available for use. Furthermore, the destructive testing generates waste that must be disposed in a proper manner, increasing material handling and storage costs.

Accordingly, there is a need to non-destructively measure resistance changes in materials, such as nuclear fuel rod cladding.

SUMMARY

The invention described herein achieves the above needs through the apparatus and method described.

The present invention provides a method of measuring an electrical resistance change in a nonferrous material. The method includes the steps of: providing a nonferrous material, inducing a magnetic field from the nonferrous material, measuring the remote magnetic field of the nonferrous material and comparing the measured remote field to a standard.

The present invention provides a method of measuring the electrical resistance of a nonferrous material. This method for measuring the electrical resistance of a material includes the steps of providing a nonferrous material; inducing a magnetic field from the nonferrous material; measuring the remote magnetic field of the nonferrous material and calculating the resistance of the nonferrous material.

The present invention also provides an apparatus for measuring a resistance or resistance change in a nonferrous material using remote field eddy current technology. The apparatus includes a receiving coil circuit having an eddy current instrument connected to a Remote Field Testing (RFT) receiving coil. The apparatus also includes an Outside Diameter (OD) circuit comprising an amplifier connected to an Outside Diameter Remote Field Testing (OD RFT) exciter coil arrangement and a frequency generator.

DETAILED DESCRIPTION

The present invention employs remote eddy current technology to determine resistance and resistance changes in nonferrous materials. Traditionally, remote eddy current technology employs the use of magnetic fields to determine the presence of defects in ferromagnetic materials. In the present invention, modification and adaptation of eddy current technology allows a user to measure resistance and detect differences in material resistance in nonferrous materials as compared to a calibrated standard. The resulting difference can then be used to evaluate parameters such as hydrogen accumulation in the material.

Figure 1:
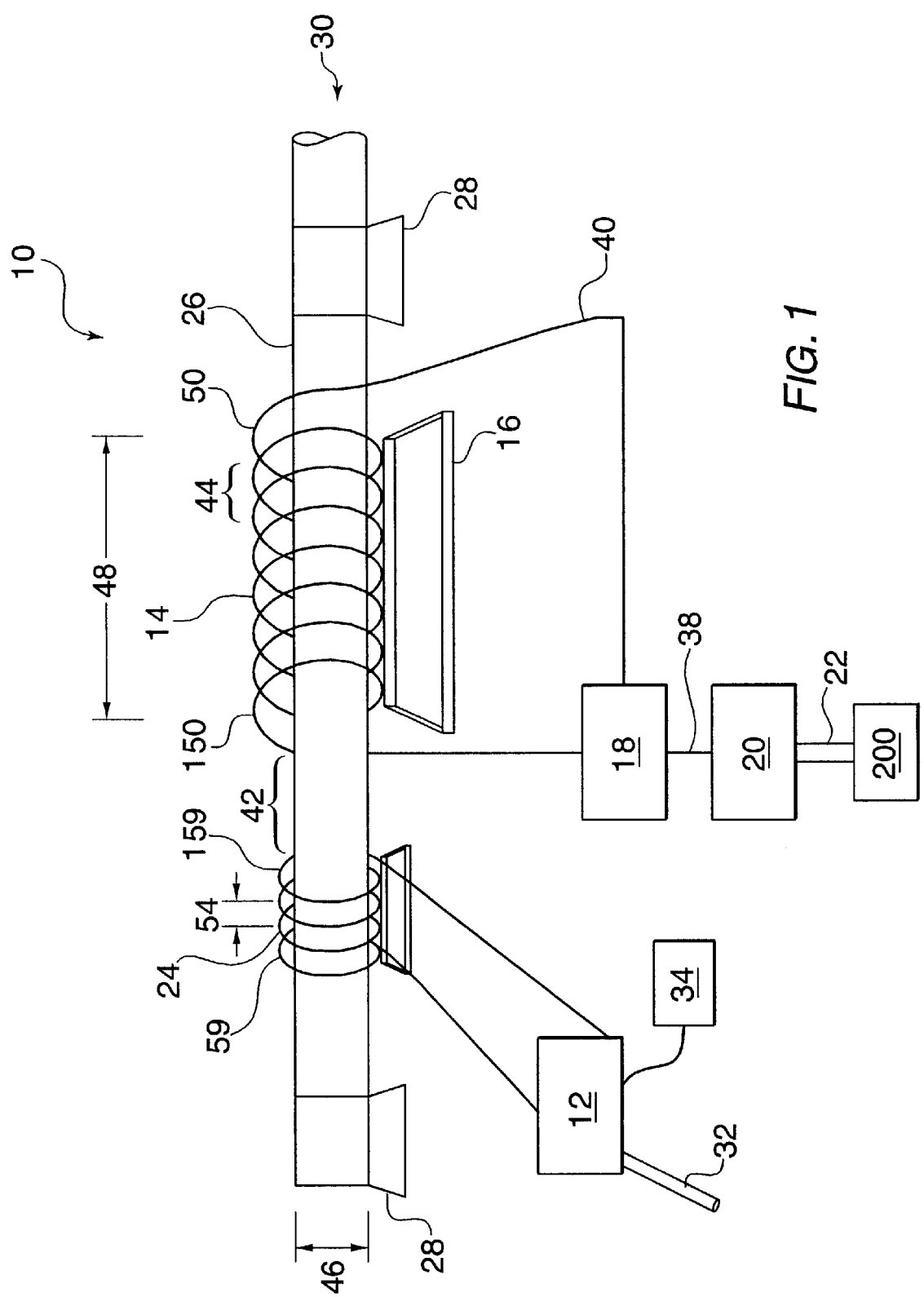
FIG. 1 shows a side view of the proposed invention in conformance with an example embodiment.

FIG. 1 shows a system 10 for measuring a resistance and calculating a resistance change in nonferrous materials. The system 10 includes: an OD circuit 40 which has an OD RFT exciter coil arrangement 14 connected to an amplifier 18 and a frequency generator 20. The system also includes a RFT receiving coil circuit 56 which includes an eddy current instrument 12 connected to a RFT receiving coil 24. In the system 10, a material that requires evaluation is placed into an OD RFT exciter coil arrangement 14 and a RFT receiving coil 24 in a direction 30 as shown. Although shown as a rod 26 in FIG. 1, the material inserted may be any shape and length. The rod 26 is optionally supported by a set of supports 28. The OD RFT exciter coil arrangement 14 and RFT receiving coil 24 are optionally supported by a fixture 16 and a RFT receiving coil support 36 respectively. Both the set of supports 28 and the fixture 16 are constructed from materials that will minimally affect generation and reception of magnetic fields.

A power source 200 connects to a frequency generator 20 through an input power cable 22. The frequency generator 20 accepts current from the power source 200 and provides current at a user defined frequency to an amplifier 18 by way of a frequency output cable 38. In operation, the frequency generator 20 may accept any input current and create an alternating current power flow through the OD circuit 40. Typical frequency ranges for the frequency generator 20 is 1 kHz to 30 kHz. Alternative ranges are possible. The above range only describes one possible embodiment of the invention. The invention is not limited to the above described range.

The amplifier 18 receives the output from the frequency generator 20 and amplifies the current to a desired level. Although shown in FIG. 1 as having a frequency generator 20 and amplifier 18 in a specific arrangement, it is possible for other configurations to exist and FIG. 1 should not be considered limiting. Other configurations exist, for example, such as providing power at a desired frequency directly to the OD circuit 40 at desired amplification levels.

The OD RFT exciter coil arrangement 14 ends 50 and 150 receive current at a voltage and frequency from amplifier 18 forming the circuit 40. As shown, the arrangement 14 has a configuration of an elongated set of loops, however other configurations of the arrangement 14 are possible. The wire gauge is chosen in relation to the power level chosen for the OD circuit 40. Wire gauge and material types are specified to reduce heating of the OD RFT exciter coil arrangement 14 and the OD circuit 40 at full power levels. The number of loops in the OD RFT exciter coil arrangement 14 must be at least one. Factors determining the number of loops include the diameter 46 of the rod 26, the desired analysis volume 48 and the current and voltage levels of the OD circuit 40. The OD RFT exciter coil output end 50 receives current at a specified voltage and frequency from the OD RFT exciter coil arrangement 14 and transmits them to the amplifier 18 completing the circuit 40.

In a receiving section of the system 10, an eddy current instrument 12 connects to a RFT receiving coil 24. An input power cable 32 provides current to the eddy current instrument 12. The eddy current instrument 12 may be of the type used for internal piping inspections using remote field technology when adapted to compare analysis results to a calibrated standard. The eddy current instrument 12, for example, may have keyboard or other input devices, a monitor or other visual depiction device, and a mechanism for calculating numbers, preferably a computer.

The RFT receiving coil 24 has at least one loop with an input end 59 and an output end 159. The RFT receiving coil 24 is similar to the OD RFT exciter coil arrangement 14. Although shown as a series of looped coils, other configurations and geometries are possible. The receiver loop spacing 54 and number of loops allow detection of remote magnetic fields emanating from the rods induced eddy current flow. To receive these remote magnetic fields, the RFT receiving coil 24 is placed at a set off distance 42 from the OD RFT exciter coil arrangement 14. Wire gauge and material type of the RFT receiving coil 24 and the RFT receiving coil circuit 56 are chosen to minimize resistance for signals received resulting from OD RFT exciter coil arrangement 14 excitation. The output end 159 of the RFT receiving coil 24 may connect to the eddy current instrument 12, as shown in FIG. 1 or may be connected to other equipment including but not limited to amplifiers, frequency analyzers, etc. An output device 34 may be connected to the eddy current instrument 12 to provide analysis output. The output device 34 is any type of device that will allow transfer of data to the user of the system 10. The device 34 may be, for example, a monitor, printer, or computer input/output device.

Operationally, the system 10 uses remote field testing eddy current technology for measuring electrical resistance and electrical resistance changes from a standard for nonferrous materials. In an example embodiment, the invention measures the mean hydrogen concentration over a large volume (typically 5–8 inches of length for a fuel rod 26) dictated by the analysis volume 48. The measurement of a mean resistance and resistance change over a large analysis volume allows calculation and detection of small electrical resistance changes in material. Typical frequency during analysis is approximately 1 kHz–30 kHz providing a stable and reliable reading during analysis.

The frequency generator 20 receives current from a power source 200 through the input power cable 22. Batteries or similar devices may also supply power allowing the system 10 to be mobile in nature. The current exits the frequency generator 20 at a specific frequency chosen by the user. The user may also define a frequency range at which material evaluation will occur. An amplifier 18 amplifies the current. The current, now at a specified voltage and frequency flows through the OD RFT exciter coil arrangement 14 and the OD RFT exciter coil circuit 40. The coil ends 50 and 150 of the OD RFT exciter coil arrangement 14 reconnect to amplifier 18 allowing electrical current flow completing the circuit 40. When energized, the moving electrons in the circuit 40 produce a magnetic field. The magnetic field induces electrons to flow in materials located in close proximity to the OD RFT exciter coil arrangement 14. In this case, electrons flow in the rod 26 from the magnetic field emanating from the OD RFT exciter coil arrangement 14. The flowing electrons on the rod 26, called eddy currents, in turn produce their own magnetic field. The magnetic field from the rod 26 is in direct opposite orientation to the OD RFT exciter coil arrangement 14 magnetic field.

Figure 2:
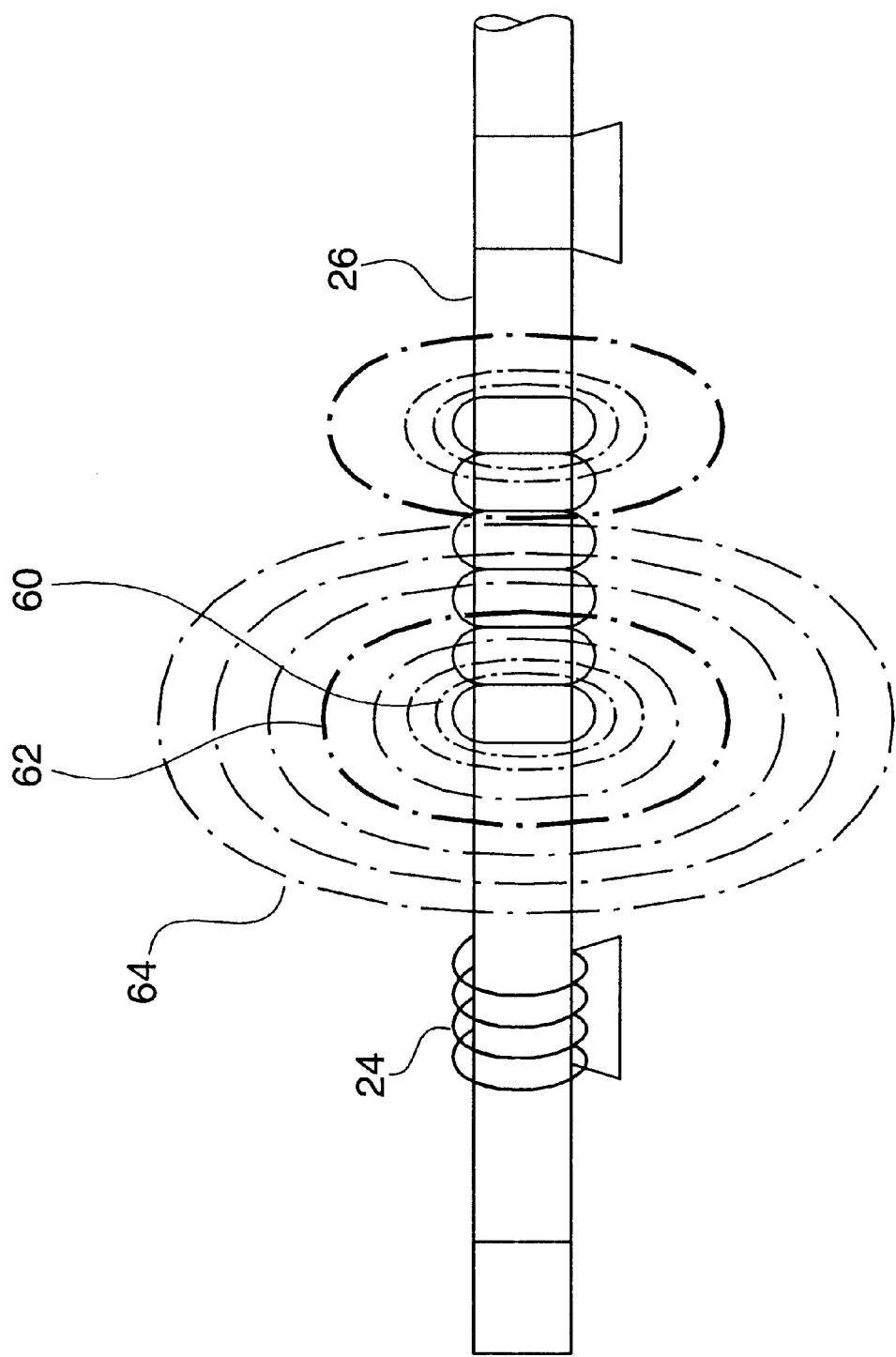
FIG. 2 shows an illustrative depiction of magnetic flux lines emanating from an excited rod arrangement of FIG. 1.

Referring to FIG. 2, the magnetic field produced by the rod 26 has three different and distinctive zones. The zones include the near field 60, a transition zone 62, and a remote field 64. The near magnetic field 60 produced by the rod 26 is characterized by an axial direction of magnetic flux that is a relatively close to the excited rod 26 component. In general, near field 60 magnetic lines of flux are located in close proximity to the OD RFT exciter coil arrangement 14 and do not pass through the wall of the nonferrous material. The transition zone 62 is a discrete area where magnetic field flux lines transition from the near field 60 to a remote field 64.

The remote field 64 may be monitored a relatively long distance from the excitation source as compared to the near field 60. This remote field 64 also travels through materials such as the rod 26. In the depicted FIG. 2, the receiver coil 24 is positioned at a set off distance 42 such that it will only receive the magnetic field from the remote field 64. Variations of the properties of the zones are allowed based upon the intensity of the induced eddy currents used.

Referring to FIG. 1, the remote field 64 induces a current to flow in the RFT receiving coil circuit 56. As is known in the art, the magnitude and phase of the eddy currents of the rod 26 will affect the current flow in the RFT receiving coil 24 as well as its impedance. The induced magnetic field in the receiving coil circuit 56 also has a significant phase shift as compared to the OD RFT arrangement 14 magnetic field. The eddy current instrument 12 monitors the induced current flow in the receiving coil circuit 56 and compares the measured current to a calibrated standard. The eddy current instrument 12 may conduct as many samples as needed to compare the measured current to the calibrated standard. Power to the eddy current instrument 12 may be through an external power supply or may be through portable batteries allowing system mobility. Although not limited to a specific sampling rate, the eddy current instrument 12 typically samples at 1000 cycles per second. The difference in the standard current compared to actual current measured is then converted to a resistance for the material in question. Knowledge of the geometry and analysis volume 48 of the rod 26, the impedance of the RFT receiving coil 24, the gage and material type of the RFT receiving coil circuit 56, the impedance and power operational levels of the OD RFT arrangement 14, and the conductivity and permeability of the rod 26 allow for calculation of the expected current. Actual measurement of the current flow allows calculation of a mean electrical resistance value for the analysis volume 48. This resistance is compared to a database of expected values stored in the eddy current instrument 12. A difference in the expected verses measured electrical resistance may then be converted to a concentration of materials incorporated into the nonferrous material. In the case of Zircaloy, for example, resistance differences of approximately 0.15 u ohms-cm occur from 500 parts per million-hydrogen incorporation. By defining the total analysis volume 48 through the loop spacing 44, accurate values of hydrogen concentration for the rod 26 are determined. The voltage induced in the RFT receiving coil 24 is proportional to the change of the flux in the excited specimen. Those skilled in the art will recognize that other factors may change the proportionality of the voltage response, and that the purely proportional relationship is considered an example and should not be considered the only embodiment or relationship possible. The disclosed invention may be equally applicable for measuring resistance changes in a variety of nonferrous materials.

Figure 3:
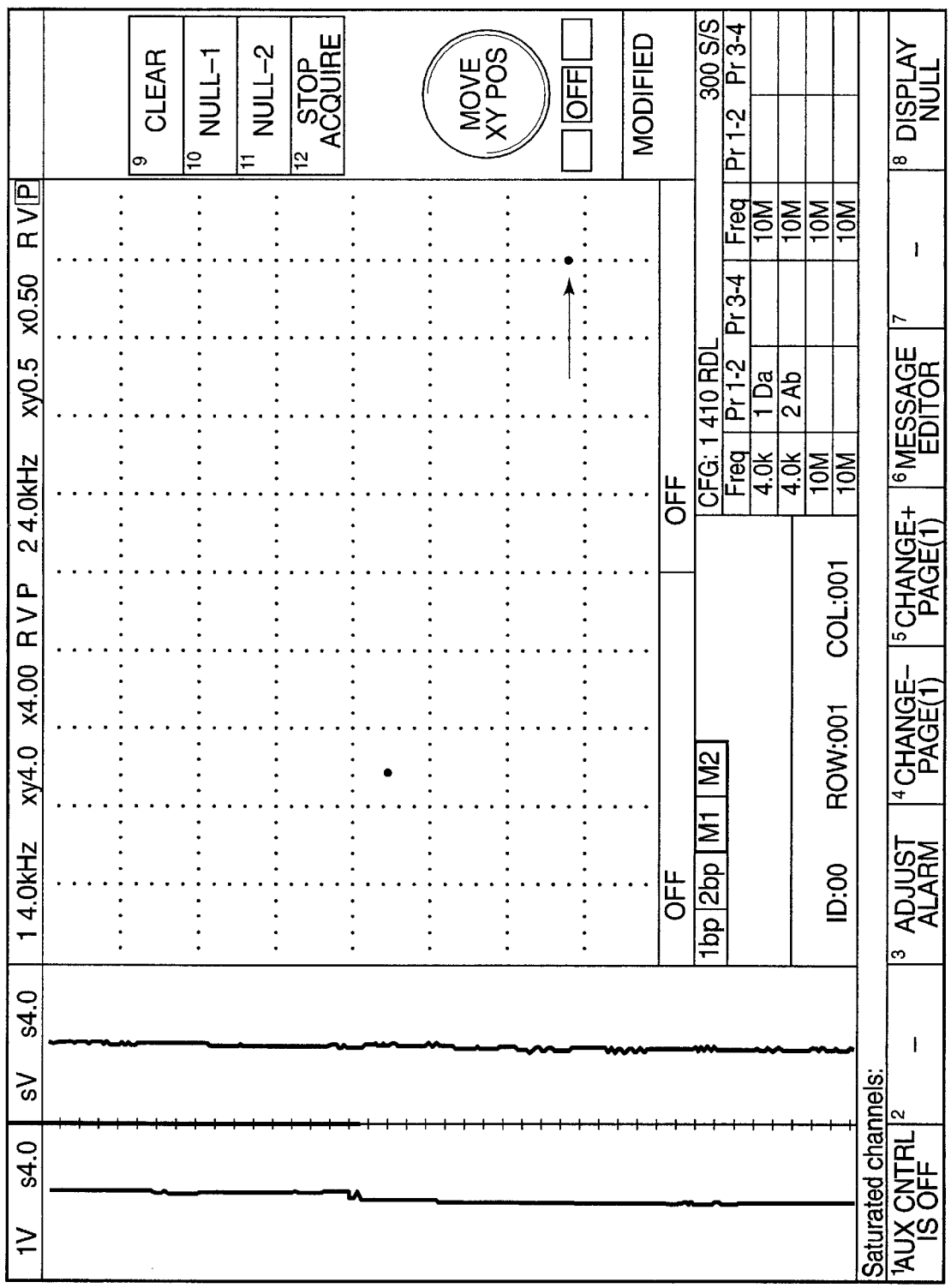
FIG. 3 shows a vector plot of cladding containing 103 parts per million hydrogen.
Figure 4:
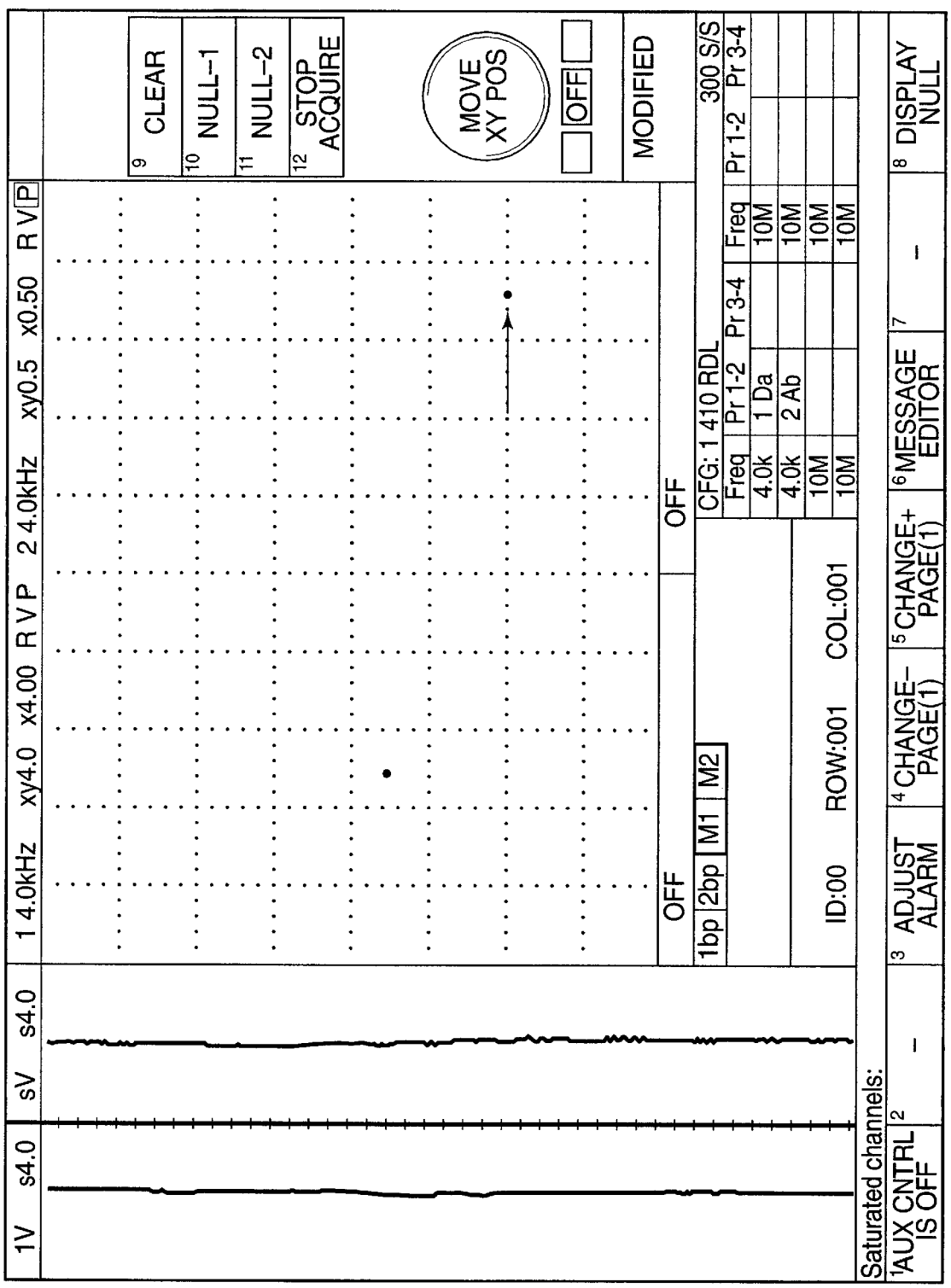
FIG. 4 shows a vector plot of cladding containing 496 parts per million hydrogen.
Figure 5:
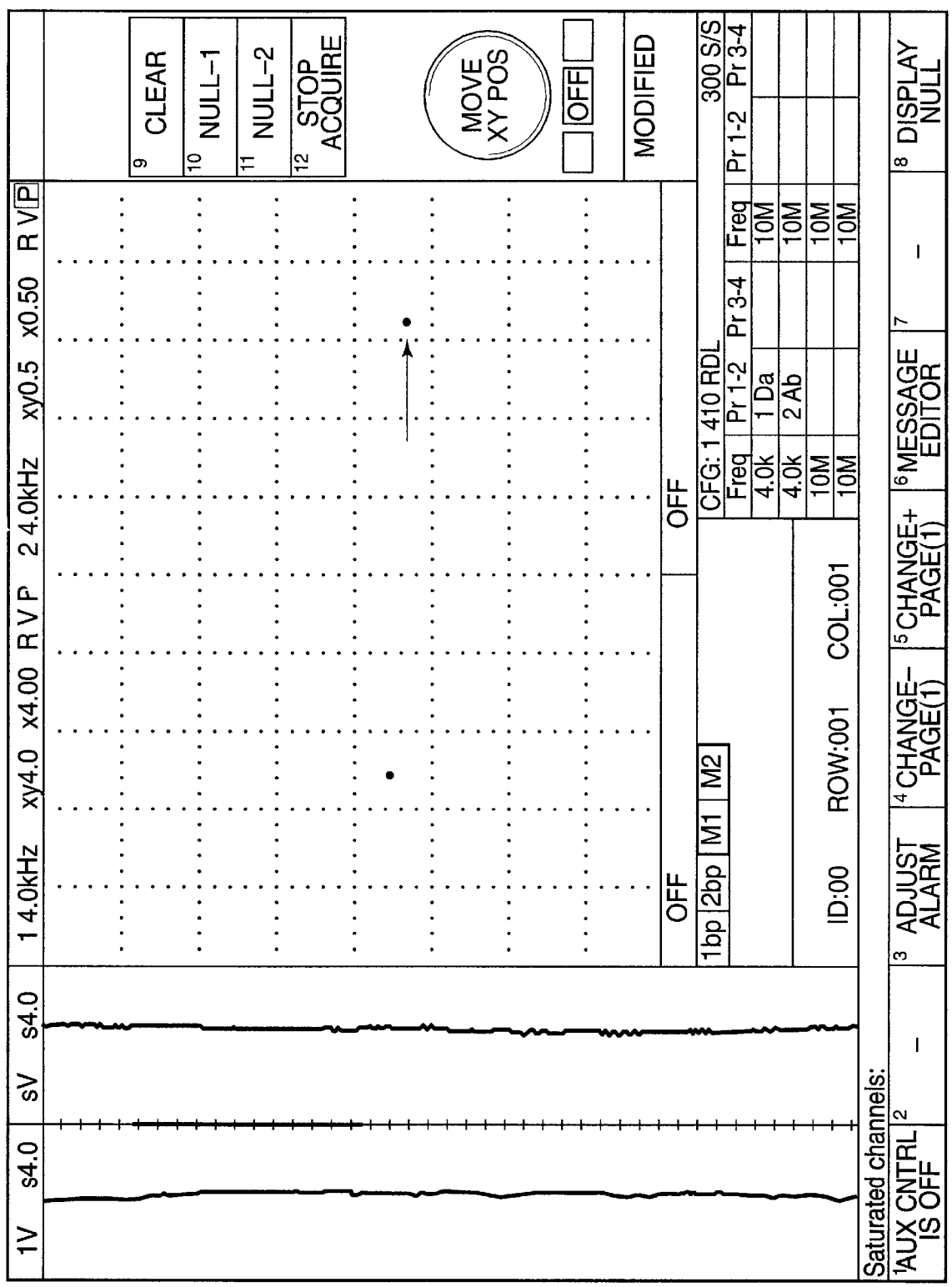
FIG. 5 shows a vector plot of cladding containing 1089 parts per million hydrogen.

Results may be displayed on an output device 34 for later analysis. Output may be produced on a voltage plane polar plot or other schematic representation generated to indicate hydrogen accumulation. Referring to FIGS. 3, 4, 5, output plots generated by the eddy current instrument 12 are shown. Measurement of the vector difference between data points indicates the presence and concentration of hydrogen accumulation in the test sample.

Readout of the eddy current instrument 12 and the output device 34 may be performed from a remote location allowing evaluating personnel to measure potentially highly radioactive components in safety. For highly radioactive component measurement, appropriate adjustments to the sensitivity of the RFT receiving coil circuit 56 may be performed through the eddy current instrument 12 or other equipment.

While the principles of the invention have been described above in connection with specific apparatus, it is to be clearly understood that this description is made only by way of example and not as a limitation on the scope of the invention.

What is claimed is:

1. A method for measuring hydrogen accumulation of a material comprising:

providing a nonferrous material from a nuclear fuel rod;

inducing a magnetic field from the nonferrous material to produce a remote magnetic field;

measuring the remote magnetic field of the nonferrous material;

comparing the measured remote magnetic field to a previously measured remote magnetic field standard of a nonferrous material without hydrogen incorporation to determine a change in electrical resistance between the standard and the nonferrous material; and calculating a hydrogen accumulation in the nonferrous material from the change in the electrical resistance.

2. The method of claim 1, further comprising calculating a difference between the measured remote magnetic field and the standard.

3. The method of claim 2, further comprising providing an output of the calculated difference between the measured remote magnetic field and the standard.

4. The method of claim 1, further comprising measuring the frequency of the remote magnetic field of the nonferrous material.

5. The method of claim 1, wherein the providing the nonferrous material includes remotely inserting the nonferrous material into an OD coil circuit and a receiving coil circuit.

6. The method of claim 1, wherein the inducing a magnetic field on the nonferrous material occurs between a frequency of 1 kHz and 30 kHz.

7. An apparatus for measuring hydrogen accumulation in a material from a resistance or the change in resistance of a material comprising:

a receiving coil circuit comprising an eddy current instrument connected to a RFT receiving coil, the receiving coil circuit configured to determine an incorporation of hydrogen from one of the resistance and the change in resistance; and an OD circuit comprising an amplifier connected to an OD RFT exciter coil arrangement and frequency generator wherein the receiving coil circuit and the OD circuit are configured to be placed in relative position to one another for sensing of a remote magnetic field generated from the OD circuit.

8. The apparatus of claim 7, further comprising a fixture, the fixture supporting the OD RFT exciter coil arrangement.

9. The apparatus of claim 7, further comprising a coil support, the coil support supporting the RFT receiving coil.

10. The apparatus of claim 7, wherein the eddy current instrument has a data input and memory capability to store standard resistance values of material.

11. The apparatus of claim 7, further comprising an output device on the receiving coil circuit.

12. The apparatus of claim 11, wherein the output device is a monitor.

13. The apparatus of claim 11, wherein the output device is a printer.

14. The apparatus of claim 7, further comprising at least one battery connected to the eddy current instrument.

15. The apparatus of claim 7, further comprising at least one battery connected to the OD circuit.

* * * * *